United States Patent [19]

James

[11] 4,210,150
[45] Jul. 1, 1980

[54] MINIATURIZED TRANSCUTANEOUS NERVE STIMULATING DEVICE

[75] Inventor: Donald N. James, Estes Park, Colo.

[73] Assignee: Staodynamics, Inc., Longmont, Colo.

[21] Appl. No.: 810,126

[22] Filed: Jun. 27, 1977

[51] Int. Cl.² ............................................. A61N 1/36
[52] U.S. Cl. .................................................. 128/421
[58] Field of Search .................. 128/419 R, 421, 422, 128/423

[56] References Cited

U.S. PATENT DOCUMENTS

| | | | |
|---|---|---|---|
| 3,077,884 | 2/1963 | Batrow et al. | 128/423 |
| 3,255,753 | 6/1966 | Wing | 128/421 |
| 3,373,747 | 3/1968 | Tapper | 128/422 |
| 3,518,996 | 7/1970 | Cortina | 128/422 |
| 3,589,370 | 6/1971 | McDonald | 128/422 |
| 3,648,708 | 3/1972 | Haeri | 128/422 |
| 4,014,347 | 3/1977 | Halleck et al. | 128/422 |
| 4,019,519 | 4/1977 | Geerling | 128/422 |
| 4,057,069 | 11/1977 | Dorffer et al. | 128/421 |
| 4,093,975 | 6/1978 | Roberts | 128/419 R X |

FOREIGN PATENT DOCUMENTS 2109085  9/1971  Fed. Rep. of Germany ........... 128/422

*Primary Examiner*—Lee S. Cohen
*Attorney, Agent, or Firm*—O'Rourke & Harris

[57] ABSTRACT

A miniaturized transcutaneous nerve stimulator is disclosed that utilizes a single 1.25 volt battery as the power source, yet provides a 30 volt DC power output over an extended period of time. The battery is connected to the primary winding of a step-up transformer with the primary also having a transistor connected in series therewith. The secondary winding of the transformer is connected with a full wave diode bridge circuit and a 30 volt Zener diode. Pulsing circuitry is also provided which includes a pulse rate and pulse width establishing multivibrators which are coupled through a buffer to a pair of Darlington amplifiers, which are also connected with the Zener diode and full wave diode bridge circuit. The output from the stimulator is coupled from the Darlington amplifiers, which amplifiers have a charging circuit connected therewith, to output terminals connectable with electrodes engagable with the skin surface of the subject.

7 Claims, 1 Drawing Figure 4,210,150

MINIATURIZED TRANSCUTANEOUS NERVE STIMULATING DEVICE

FIELD OF THE INVENTION

This invention relates to a transcutaneous nerve stimulating device and more particularly, to a miniaturized transcutaneous nerve stimulating device.

BACKGROUND OF THE INVENTION

It is known that pain can be relieved by electrical nerve stimulation devices. Such devices can be utilized by positioning electrodes on the skin surface of the subject and then applying electrical energy, most often by pulses, to the electrodes.

Numerous prior art devices have been heretofore suggested and/or utilized for accomplishing this end, and among such devices is U.S. Pat. No. 4,014,347 which has proven to be quite useful for pain suppression over extended periods of time.

As a further addition to such transcutaneous nerve stimulators, a miniaturized stimulating device was thought to be needed, with such device being simple yet dependable.

SUMMARY OF THE INVENTION

This invention provides a miniaturized transcutaneous nerve stimulator that is simple yet dependable and can be used for long periods of time. The device is powered by a single 1.25 volt battery and yet provides up to a 30 volt output pulse. A transistor is utilized in series with the primary winding of a step-up transformer and Darlington amplifiers connected with a charging circuit are utilized to receive a 30 volt DC charge and pulse rate and pulse width establishing multivibrator outputs.

It is therefore an object of this invention to provide an improved transcutaneous nerve stimulator.

It is another object of this invention to provide an improved transcutaneous nerve stimulator that is miniaturized.

It is still another object of this invention to provide an improved transcutaneous nerve stimulator that is powered by a low voltage source yet provides a high voltage pulse output over extended periods of time.

It is yet another object of this invention to provide an improved transcutaneous nerve stimulator that utilizes a transistor in series with a step-up transformer powered from a low voltage battery source.

It is yet another object of this invention to provide an improved trancutaneous nerve stimulator that includes a pair of Darlington amplifiers connected with a charging circuit at the output stage.

With these and other objects in view, which will become apparent to one skilled in the art as the description proceeds, this invention resides in the novel construction, combination, and arrangement of parts substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawing illustrates a complete embodiment of the invention according to the best mode so far devised for the practical application of the principles thereof and in which the single FIGURE is an electrical schematic diagram of the transcutaneous nerve stimulator of this invention.

DESCRIPTION OF THE INVENTION

Figure 1:
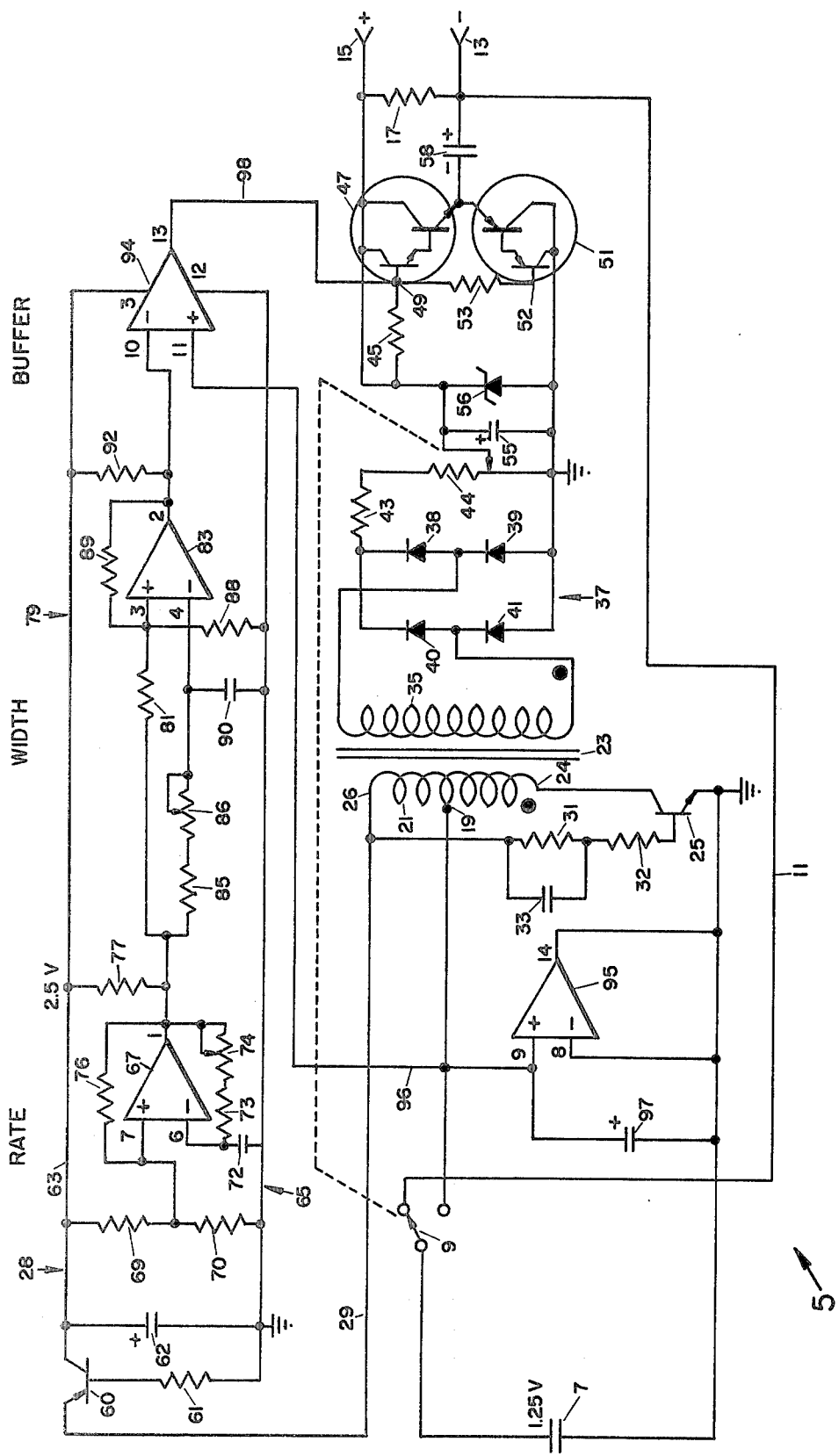

Referring now to the drawings, the transcutaneous nerve stimlating device 5 of this invention is powered by a 1.25 volt battery 7, which battery is preferably a nickel-cadmium battery. The battery is grounded at the negative side and has the positive side connected with 2-position switch 9. Switch 9 serves as an off-on switch with the switch contactor when in the off-position (as shown in the drawings) being connected by lead 11 to the negative electrode output 13 and to the positive electrode output 15 through resistor 17 of a charging circuit. The contactor of switch 9, when in the on-position, is connected to the center tap 19 of the primary winding 21 of transformer 23.

One side 24 of primary winding 21 of transformer 23 is connected to the collector of transistor 25, the emitter of which transistor is grounded. The other side 26 of the primary winding 21 is connected to pulse producing circuitry 28 through lead 29 and through series connected resistors 31 and 32 to the base of transistor 25, with resistor 31 having a capacitor 33 connected in parallel therewith so that resistors 31 and 32 and capacitor 33 allow a positive feedback to transistor 25 to insure oscillation and therefore an AC waveform on the primary 26 of transformer 23. As is brought out hereinafter, the waveform coupled from transformer 23 is rectified at diode bridge rectifier 37 and the resulting rectified output coupled through resistor 43 and the moveable tap of potentiometer 44 to capacitor 55.

The secondary winding 35 of transformer 23 is connected at opposite ends through opposite sides of a full wave diode bridge rectifier 37, which rectifier includes diodes 38, 39, 40 and 41. The junction of diodes 39 and 41 is grounded while the junction of diodes 38 and 40 is connected through resistor 43, potentiometer 44, and resistor 45 to an input (designated by numeral 49) to Darlington amplifier 47, with a second Darlington amplifier 51 having an input (designated by numeral 52) connected to resistor 45 through resistor 53. The movable tap of potentiometer 44 is connected with the plus electrical terminal 15, one side of capacitor 55 and 30 volt Zener diode 56, while the other side of both the capacitor and Zener diode are grounded. The negative electrode terminal 13 is connected to a common output junction of the Darlington amplifiers 47 and 51 through capacitor 58, which capacitor along with resistor 17 forms a charging circuit in that capacitor 58 provides a pulse coupling means to the negative electrode 13 and resistor 17 insures that no charge is allowed to build up on capacitor 58 to thus insure a net zero volt DC between positive electrical terminal 15 and negative electrical terminal 13. Darlington amplifiers 47 and 51 are utilized for switching under the control of the pulses received from the pulse producing circuitry.

The emitter of transistor 60 is connected to lead 29 with the base of the transistor being connected to ground through resistor 61. The collector of transistor 60 provides a 2.5 volt output on lead 63 for the pulse producing circuitry 28 and has a bypass capacitor 62 to ground. DC voltage is thus provided to the multivibrators.

Rate pulsing is provided by multivibrator 65 which includes amplifier 67, the plus input (pin 7) of which is connected to the junction or resistors 69 and 70 (connected between leads 63 and ground as a voltage divider) and a negative input (pin 6) of which is connected with ground through capacitor 72, and with the output (pin 1) of the amplifier through resistor 73 and potentiometer 74. The output (pin 1) of the amplifier is also connected with the junction of resistors 69 and 70 through resistor 76 and to lead 63 through resistor 77.

Pulse width determintation is made by multivibrator 79. The output from multivibrator 65 is coupled from pin 1 of amplifier 67 through resistor 81 to the plus input (pin 3) of amplifier 83 and through resistor 85 and potentiometer 86 to the negative input (pin 4) of amplifier 83. The plus input (pin 3) of amplifier 83 is connected with ground through resistor 88 and to the output (pin 2) through resistor 89, while the negative input (pin 4) is connected to ground through capacitor 90. In addition, the output (pin 2) of amplifier 83 is connected to lead 63 through resistor 92.

The output from mulivibrator 79 is coupled from pin 2 of amplifier 83 to the negative input (pin 10) of buffer amplifier 94. The plus input (pin 11) of amplifier 94 is connected to the plus input (pin 9) of amplifier 95 through lead 96. Pin 9 of amplifier 95 is connected with ground through capacitor 97, while the negative input (pin 8) and output (pin 14) are directly grounded. Amplifier 95 is a part of integrated circuit LM339N which also includes amplifiers 67, 83, and 94, and amplifier 95 is connected in the circuit to prevent spurious operation of amplifier 94. The output (pin 13) from buffer amplifier 94 is coupled by lead 98 to junction 49 (and through resistor 53 to junction 52) of the Darlington amplifiers. The charge on capacitor 55 is determined by the setting of the moveable tap of potentiometer 44 to which it is connected, and the pulse amplitude at lead 98 is determined by the charge on capacitor 55 through resistor 45.

The unit of this invention has been successfully miniaturized and a working embodiment of the unit has been reduced so that a housing with dimensions of about 2.375"×1.93"×0.715" is utilized.

In a working embodiment of this invention, the following components have been utilized, but it is meant to be realized that the invention is not to be limited to the exact components shown by way of illustration:

Resistors (ohms): 17-470K; 31-1K; 32-330; 43-10K; 45-10K; 53-4.7K; 61-15K; 69-1M; 70-240K; 73-75K; 76-470K; 77-417K; 81-200K; 85-12K; 88-82K; 89-750K; and 92-10K.

Potentiometers: 44-0 to 1 Meg; 74-0 to 250 K; and 86-0 to 100K

Capacitors (mfd): 33-0.022; 55-4.7 (35 v); 58-4.7 (35 v); 62-10 (4 v); 72-0.047; 90-0.0022; and 97-10 (4 v).

Transistors: 25-MPS 6531; and 60-2N3905.

Diodes: 38-41 —1N914

Zener diode 56—1N4751 (30 volt)

Transformer 23—ITC 1052-6

Amplifiers 67, 83, 94 and 95—LM339N

Darlington Amplifiers: 47-MPA13 and 51-MPSA65

In operation, skin contact electrodes are connected by electrical leads to the output terminals of the transcutaneous nerve stimulator of this invention. The unit is switched to the on-position, after which the potentiometer controls are varied until the pain subsides. The unit is then utilized to prevent the pain sensation for as long as needed (control adjustments being adjusted as required). The unit will continue to operate until the battery runs down to about 0.85 volts.

From the foregoing, it can be appreciated that this invention provides an improved transcutaneous nerve stimulating device that is miniaturized yet dependable for use.

What is claimed is:

1. In a transcutaneous nerve stimulating device having electrodes for applying electrical energy to a subject, an electrical unit comprising:

switching means;

pulse producing means for generating pulses having predetermined widths and at a predetermined rate, said pulse producing means being connected with said switching means for coupling said generated pulses thereto;

rectifier means connected with said switching means;

a very low voltage source of below two volts;

electrical power means including a step-up transformer the primary winding of which is connected with said very low voltage source and directly connected with said pulse producing means to supply power thereto, and the secondary winding of which is connected with said rectifier means; and output terminals connected with said switching means and through which pulses may be coupled to the electrodes of said device for application to a subject.

2. The electrical unit of claim 1 wherein said switching means includes a pair of Darlington amplifiers, and wherein said Darlington amplifiers have a charging circuit connected therewith.

3. The electrical unit of claim 1 wherein said entire primary winding of said step-up transformer has a transistor connected in series therewith, and wherein said very low voltage source is a 1.25 volt battery.

4. In a transcutaneous nerve stimulating device having electrodes engagable with the skin of a subject for applying electrical energy to the subject, an electrical unit, comprising:

amplifying means having a charging circuit connected therewith and providing an output for coupling to the electrodes of said transcutaneous nerve stimulating device;

pulse producing means for generating pulses having a predetermined width and at a predetermined rate, said pulse producing means being connected with said amplifying means for coupling said generated pulses thereto;

rectifier means connected with said amplifying means;

a step-up transformer having a primary winding and a secondary winding connected with said rectifier means;

a transistor connected in series with the entire primary winding of said transformer;

a battery having a very low voltage of about 1.25 volts, said battery being connected to said primary winding of said step-up transformer; and means for directly connecting said battery with said pulse producing means to provide DC bias thereto.

5. The electrical unit of claim 4 wherein said amplifying means includes a pair of Darlington amplifiers, wherein said rectifier means includes a full wave diode bridge circuit, and wherein said unit includes a 30 volt Zener diode connected with said full wave diode bridge circuit.

6. The electrical unit of claim 4 wherein said pulse producing means includes a first multivibrator to provide a pulse rate control output, a second multivibrator connected with said first multivibrator to produce a pulse width control output, and a buffer amplifier connected between said second multivibrator and said amplifying means.

7. A transcutaneous nerve stimulating device, comprising: output terminal means adapted to be connected with electrodes positionable in skin contact to apply electrical energy to a subject;
- a charging circuit connected with said output terminal means;
- a pair of Darlington amplifiers connected with said charging circuit;
- a first multivibrator for providing a pulse rate control output;
- a second multivibrator for providing a pulse width control output, said second multivibrator being connected with said first multivibrator.
- a buffer amplifier connected between said second multivibrator and said Darlington amplifiers to supply switching signals thereto as determined by said multivibrators;
- a 30 volt Zener diode connected with said Darlington amplifiers;
- a full wave diode bridge circuit connected with said Zener diodes;
- a step-up transformer having a primary winding and a secondary winding connected with said full wave diode bridge circuit;
- a transistor connected in series with said entire primary winding of said transformer;
- a battery having a voltage of about 1.25 volts; and
- means for connecting said battery to said primary winding of said transformer and said transistor and for directly connecting said battery to said multivibrators to supply a bias voltage thereto.

* * * * *